United States Patent
Zhang (10) Patent No.: US 8,971,493 B2
(45) Date of Patent: Mar. 3, 2015

(54) SYSTEM FOR IMAGE SCANNING AND ACQUISITION WITH LOW-DOSE RADIATION

(75) Inventor: Hongxuan Zhang, Palatine, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 586 days.

(21) Appl. No.: 13/079,999

(22) Filed: Apr. 5, 2011

(65) Prior Publication Data

US 2012/0057674 A1 Mar. 8, 2012

Related U.S. Application Data (60) Provisional application No. 61/380,751, filed on Sep. 8, 2010.

(51) Int. Cl.
G21K 3/00 (2006.01)
G21K 1/04 (2006.01)
G21K 1/02 (2006.01)
H05G 1/38 (2006.01)
A61B 6/00 (2006.01)
A61B 5/00 (2006.01)
A61B 6/06 (2006.01)
A61B 5/024 (2006.01)

(52) U.S. Cl.
CPC .......... *A61B 6/503* (2013.01); *A61B 5/024* (2013.01); *A61B 5/7285* (2013.01); *A61B 6/06* (2013.01); *A61B 6/4035* (2013.01); *A61B 6/469* (2013.01); *A61B 6/507* (2013.01); *A61B 6/541* (2013.01); *A61B 6/542* (2013.01); *Y10S 378/901* (2013.01)
USPC .......... 378/95; 378/150; 378/151; 378/158; 378/165; 378/901

(58) Field of Classification Search
USPC .......... 378/8, 20, 91, 95, 147, 149–153, 157, 378/158, 204, 205, 210, 901, 62, 63, 165; 382/128, 130–132; 600/301, 425, 428, 600/481, 484, 485, 508, 509, 521, 523, 529, 600/561
See application file for complete search history.

(56) References Cited

U.S. PATENT DOCUMENTS

| 3,871,360 A | * | 3/1975 | Van Horn et al. ............. 600/484 |
| 5,199,438 A | | 4/1993 | Pearlman |
| 5,229,668 A | | 7/1993 | Hughes et al. |
| 5,565,914 A | | 10/1996 | Motta |
| 5,590,649 A | | 1/1997 | Caro et al. |
| 5,778,294 A | | 7/1998 | Hiraoka et al. |
| 5,818,902 A | * | 10/1998 | Yu .................................. 378/65 |

(Continued)

*Primary Examiner* — Anastasia Midkiff (57) ABSTRACT

A medical imaging system adaptively acquires anatomical images using a shape adaptive collimator including multiple different portions of X-ray absorbent material automatically adjustable to alter the dimensions of a spatial cross section of an X-ray beam of radiation into a non-rectangular shape, in response to a control signal. The synchronization processor provides a heart rate related synchronization signal derived from a patient cardiac function related parameter. The synchronization signal enables adaptive variation in timing of image acquisition within an individual heart cycle and between successive heart cycles of each individual image frame of multiple sequential image frames. The X-ray image acquisition device uses the shape adaptive collimator for acquiring anatomical images of the region of interest with reduced patient X-ray exposure in response to the synchronization signal. A display processor presents resultant images.

21 Claims, 8 Drawing Sheets

(56) References Cited

U.S. PATENT DOCUMENTS

| | | | |
|---|---|---|---|
| 5,832,051 A | 11/1998 | Lutz | |
| 5,854,656 A | 12/1998 | Noggle | |
| 5,872,572 A | 2/1999 | Rossignac | |
| 6,148,062 A | 11/2000 | Romeas | |
| 6,154,516 A | 11/2000 | Heuscher et al. | |
| 6,256,406 B1 | 7/2001 | Garland et al. | |
| 6,275,560 B1 | 8/2001 | Blake et al. | |
| 6,298,111 B1 * | 10/2001 | Ozaki | 378/8 |
| 6,393,091 B1 | 5/2002 | Slack | |
| 6,411,740 B1 | 6/2002 | Daly | |
| 6,477,553 B1 | 11/2002 | Druck | |
| 6,501,828 B1 * | 12/2002 | Popescu | 378/150 |
| 6,614,448 B1 | 9/2003 | Garlick et al. | |
| 6,708,052 B1 | 3/2004 | Mao et al. | |
| 6,795,526 B2 | 9/2004 | Walker et al. | |
| 6,873,682 B2 | 3/2005 | Francke et al. | |
| 6,993,117 B2 | 1/2006 | Toth et al. | |
| 7,031,504 B1 | 4/2006 | Argiro et al. | |
| 7,076,029 B2 | 7/2006 | Toth et al. | |
| 7,092,490 B2 | 8/2006 | Saladin et al. | |
| 7,120,231 B2 | 10/2006 | Spahn | |
| 7,142,630 B2 | 11/2006 | Suzuki | |
| 7,308,073 B2 | 12/2007 | Tkaczyk et al. | |
| 7,336,768 B2 | 2/2008 | Ogawa | |
| 7,340,032 B2 | 3/2008 | Besson | |
| 7,342,993 B2 | 3/2008 | Besson | |
| 7,426,258 B1 | 9/2008 | Zweig | |
| 7,434,998 B2 | 10/2008 | Saito | |
| 7,522,696 B2 * | 4/2009 | Imai | 378/8 |
| 7,526,065 B2 | 4/2009 | Hardesty | |
| 7,616,730 B2 * | 11/2009 | Flohr | 378/8 |
| 7,630,477 B2 | 12/2009 | Toth et al. | |
| 7,640,137 B2 | 12/2009 | Numata et al. | |
| 7,653,179 B2 | 1/2010 | Ramsauer et al. | |
| 7,680,249 B2 | 3/2010 | Yuan | |
| 2005/0069086 A1 | 3/2005 | Deych et al. | |
| 2005/0080336 A1 * | 4/2005 | Byrd et al. | 600/428 |
| 2005/0090737 A1 * | 4/2005 | Burrell et al. | 600/428 |
| 2005/0243970 A1 | 11/2005 | Bernhardt | |
| 2006/0182226 A1 | 8/2006 | Yuan et al. | |
| 2008/0267348 A1 | 10/2008 | Puusaari et al. | |
| 2008/0272309 A1 | 11/2008 | Schweizer et al. | |
| 2009/0024016 A1 * | 1/2009 | Zhang et al. | 600/381 |
| 2009/0122962 A1 | 5/2009 | Gould et al. | |
| 2009/0141856 A1 * | 6/2009 | Hsieh et al. | 378/8 |
| 2009/0312648 A1 * | 12/2009 | Zhang et al. | 600/483 |
| 2010/0056897 A1 | 3/2010 | Zhang | |
| 2010/0081917 A1 | 4/2010 | Zhang et al. | |
| 2010/0098216 A1 | 4/2010 | Dobson | |
| 2010/0111262 A1 | 5/2010 | Lee et al. | |
| 2010/0150307 A1 | 6/2010 | Grodzins | |

* cited by examiner

SYSTEM FOR IMAGE SCANNING AND ACQUISITION WITH LOW-DOSE RADIATION

This is a non-provisional application of provisional application Ser. No. 61/380,751 filed Sep. 8, 2010, by H. Zhang.

FIELD OF THE INVENTION

This invention concerns a medical imaging system and shape adaptive collimator for adaptively acquiring anatomical images with reduced patient X-ray exposure in response to adaptive variation in timing of image acquisition within an individual heart cycle and between successive heart cycles of each individual image frame of a sequence of image frames.

BACKGROUND OF THE INVENTION

Angiography (or arteriography) imaging is used to monitor and characterize cardiac tissue and functions, including morphology, blood flow, anatomy and arterial luminal size by displaying static and dynamic image silhouettes. This provides the ability to assess cardiac and coronary arterial function and to visualize a heart system (Ventricle, Atrium, Vessel), which facilitates diagnosis and determination of cardiac disease. It is desirable to minimize radiation dose used in medical imaging. Known X-ray imaging and fluoroscopic imaging typically capture images randomly or based on time and may lead to unnecessary X-ray exposure. It is known for a fluoroscopic imaging system to employ ECG or respiration signals for triggering X-ray exposure and image scanning and acquisition to avoid patient movement and unwanted electrical noise. However known image scanning and acquisition systems usually employ uniformly timed image acquisition and may fail to capture anatomical features during an ECG Q wave or S wave, for example, since the image scanning is triggered in response to an R wave.

Known image systems, such as X-ray systems, usually employ a collimator (typically a rectangle or square X-ray attenuation device) to limit X-ray beam exposure and radiation dose. However, especially in heart monitoring cases, an anatomical region of interest (ROI) area is usually not a rectangle or square which results in unnecessary radiation exposure to an area outside the ROI. Known imaging systems usually employ a fixed image scanning rate in continuous image acquisition. Known imaging systems may apply a fixed pixel resolution and radiation exposure (time interval length and intensity) in continuous image acquisition and use uniform intensity X-ray beam radiation over an entire image. A system according to invention principles addresses these deficiencies and related problems.

SUMMARY OF THE INVENTION

A system uses an adaptive adjustable image radiation filter or collimator to control non-uniform image radiation exposure and beam shape/focus and intensity, low and high dose exposure of areas in a single image and adaptive radiation dose optimization using X-ray beam spatial control and beam exposure time gating and triggering in response to hemodynamic, electrophysiological and vital sign signals. A medical imaging system adaptively acquires anatomical images using a shape adaptive collimator, a synchronization processor, an X-ray image acquisition device and a display processor. The shape adaptive collimator includes multiple different portions of X-ray absorbent material automatically adjustable to alter the dimensions of a spatial cross section of an X-ray beam of radiation into a non-rectangular shape, in response to a control signal indicating shape of a region of interest of patient anatomy. The synchronization processor provides a heart rate related synchronization signal derived from a patient cardiac function associated parameter. The synchronization signal enables adaptive variation in timing of image acquisition within an individual heart cycle and between successive heart cycles of each individual image frame of multiple sequential image frames. The X-ray image acquisition device uses the shape adaptive collimator for acquiring anatomical images of the region of interest with reduced patient X-ray exposure in response to the synchronization signal. The display processor presents images, acquired by the acquisition device to a user on a reproduction device.

DETAILED DESCRIPTION OF THE INVENTION

An imaging system improves medical imaging by capturing patient tissue images with low-dose X-ray radiation. The imaging system achieves non-uniform image scanning and acquisition with adaptive and automated control of radiation exposure timing and spatial ROI (region of interest) area. The image radiation timing is controlled and adjusted in response to patient signals (such as ECG, ICEG, Hemodynamic, and vital sign signals, for example) and radiation spatial information is determined by a user or image analysis in response to ROI selection. A programmable image radiation filter or collimator is used to accurately control non-uniform image radiation exposure by adjusting beam shape and focus and intensity as well as to determine low and high radiation dose areas in a single image and adaptive radiation dose optimization. The system reduces redundant beam scanning and determines an accurate image scanning time, provides stable image capture and cardiac tissue and function characterization (such as pathology type and severity) by X-ray beam spatial control and beam exposure time gating and triggering in response to hemodynamic, electrophysiological and vital sign signals. The system also uses patient motion noise rejection to accommodate movement associated with heart beat, respiration, body and bed shift. Furthermore, the system provides X-ray imaging by providing local ROI fast dynamic activity monitoring with low dose radiation, e.g. for studying arterial wall movement and blood contrast flow in a vessel.

The system identifies different areas in a single image for application of different levels of imaging radiation exposure based on selected ROI area. A first area of interest is imaged using a higher radiation intensity exposure to provide relatively high imaging luminance resolution and a second area of no or limited interest, is imaged using a lower radiation intensity exposure to provide relatively lower imaging luminance resolution. The system also adaptively adjusts radiation exposure based on cardiac function, such as function identified by an ECG P wave, R wave, and rest portion in a cardiac cycle to facilitate imaging of different function procedures and tissue, such as chamber activity monitoring and blood flow and to provide different image luminance resolution. The system also provides imaging of relatively fast dynamic cardiac activities and slow or rest cardiac activities in a cardiac cycle by adaptive control of X-ray scanning parameters.

The system uses non-uniform image scanning and acquisition to provide tissue function image capture, such as of blood flow in a specific vessel or cardiac chamber maximum size (for volume analysis) triggered using a blood pressure signal and also employs image capture triggering in response to a respiration signal to reduce movement associated noise. The system also acquires X-ray images in response to non-uniform time signal gating and spatial ROI selection. The non-uniform time signal gating is provided using hemodynamic signals (invasive blood pressure, non-invasive blood pressure, blood flow speed), electrophysiological signals (surface ECG, intra-cardiac electrograms, both unipolar and bipolar signals), and vital sign signals (SPO2, respiration). The system further uses spatial X-ray radiation image area selection together with non-uniform image acquisition with adaptive and automated control of radiation exposure to selected ROI (region of interest) areas in a single image based on user preference and image dynamic content. The system Image acquisition gating and synchronization is used for cardiac dynamic activity and vessel monitoring (such as LAD coronary arteries) involving use of cardiac function synchronization signals for a particular ROI area. For example, if an image study is focusing on ventricular cardiac output estimation, optimum selection of time and X-ray exposure area is performed by, using a ROI (spatial) controllable collimator to limit the exposure area to a left corner of the heart (e.g., the left ventricle region) and using non-uniform time gating to initiate X-ray exposure and image data acquisition.

Figure 1:
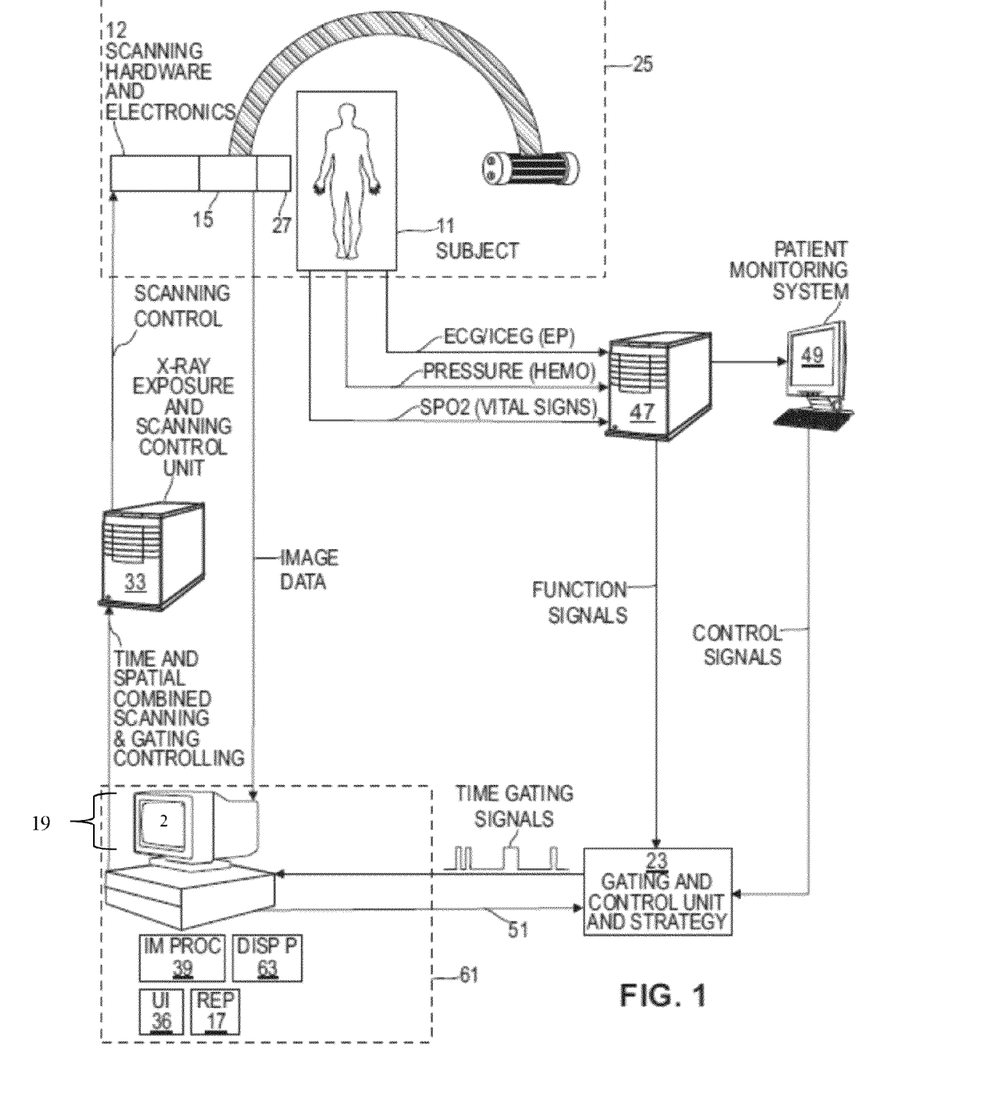
FIG. 1 shows a medical imaging system for adaptively acquiring anatomical images, according to invention principles.

FIG. 1 shows medical imaging system 10 for adaptively acquiring anatomical images. System 10 includes X-ray imaging system 25, patient monitoring system 49 and image processing system 61. Patient monitoring system 49 acquires patient monitoring signals from patient 11 via signal interface 47 including ECG, ICEG, EP signals, a blood pressure signal, vital sign and SPO2 signals used to control and trigger image acquisition and ROI selection in an image. System 10 uses the signals in synchronizing image scanning and acquisition. For example, the system uses end of diastolic and systolic signals and data indicating a ROI comprises a ventricular region, to control the X-ray radiation exposure. System 10 provides gating trigger signals using signals from patient monitoring system 49 that are partially uniform and non-uniform, depending on a clinical application. Feedback signal 51 from image processing system 61 is used by synchronization processor 23 for compensating trigger signal timing for circuit time delay. In order to lower X-ray radiation dose and reduce unnecessary exposure, in one embodiment a user manually operates X-ray imaging system 25 system to select and manipulate a ROI (region of interest). However the collimator in known image systems usually can only achieve a rectangle or square ROI. In contrast, the system advantageously enables ROI shaping of an X-ray exposure area. This ROI spatial control is achieved via manual selection (e.g. by a user employing a mouse or touch screen) or by system automatic selection.

Image processing system 61 comprises one or more processing devices (e.g., workstations or portable devices such as notebooks, Personal Digital Assistants, phones) 12 that individually include image processor 39, a user interface control device 36 such as a keyboard, mouse, touchscreen, voice data entry and interpretation device and display 19, display processor 63 and repository 17. X-ray modality system 25 provides patient X-ray medical images using a C-arm X-ray radiation source and detector device rotating about a patient table. The medical images are generated in response to predetermined user (e.g., physician) specific preferences. At least one repository 17 stores medical image studies for multiple patients in DICOM compatible (or other) data format.

X-ray imaging system 25 includes shape adaptive collimator 15 and radiation filter 27. Shape adaptive collimator 15 includes multiple different portions of X-ray absorbent material automatically adjustable to alter the dimensions of a spatial cross section of an X-ray beam of radiation into a non-rectangular shape, in response to a first control signal indicating shape of a region of interest of patient anatomy. Filter 27 includes at least one portion of X-ray filtering material automatically adjustable to attenuate X-ray radiation in response to a second control signal. Synchronization processor 23 provides a heart rate related synchronization signal derived from a patient cardiac function related parameter. The synchronization signal enables adaptive variation in timing of image acquisition within an individual heart cycle and between successive heart cycles of each individual image frame of multiple sequential image frames. X-ray imaging system 25 uses shape adaptive collimator 15 for acquiring anatomical images of the region of interest with reduced patient X-ray exposure in response to the synchronization signal. Display processor 63 presents display images 2 acquired by X-ray imaging system 25 to a user on display 19. Display processor 63 provides at least one display image 2 enabling a user to enter data indicating a shape of a region of interest of patient anatomy using an image of the patient anatomy. Controller 33 generates the first and second control signals in response to user data entry indicating, (a) a region of interest of patient anatomy and (b) a cardiac function to be investigated. Image processor 39 calculates at least one of maximum left ventricle volume and minimum left ventricle volume based on acquired image data.

Figure 2:
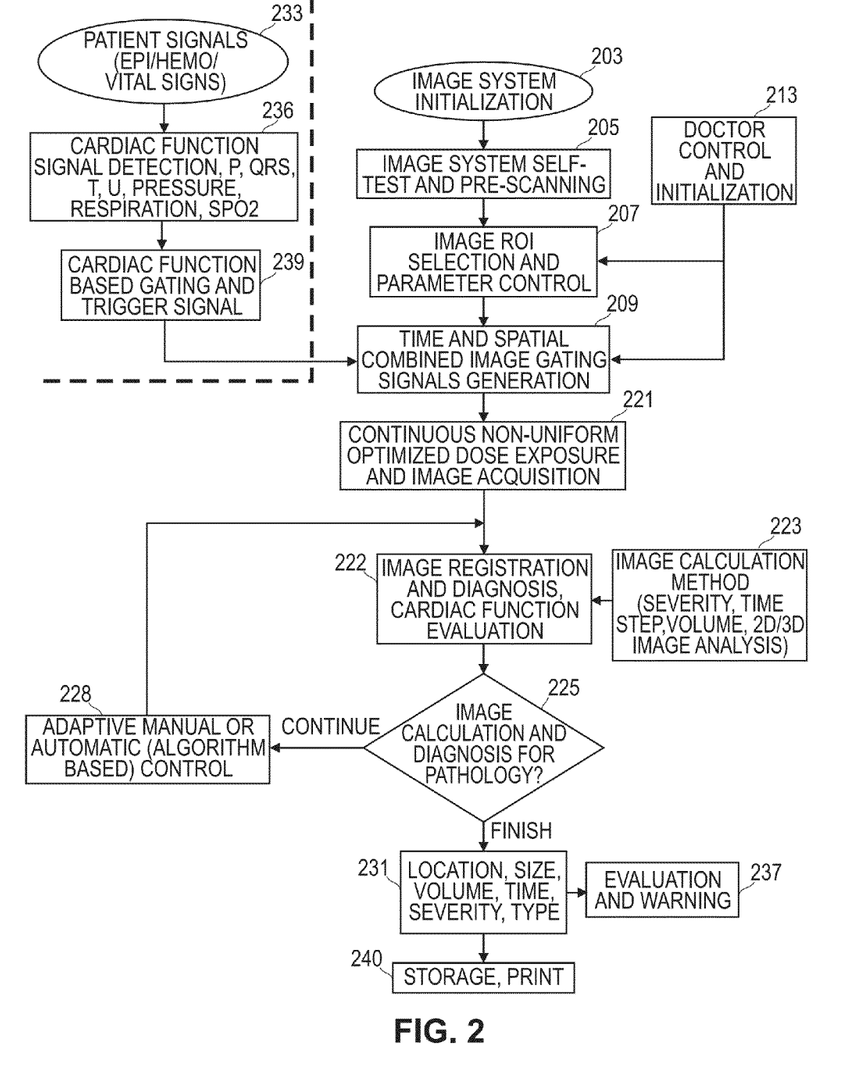
FIG. 2 shows a flowchart of a process used by a medical imaging system for adaptive non-uniform image scanning and acquisition based on time and spatial ROI selection, according to invention principles.

FIG. 2 shows a flowchart of a process used by medical imaging system 10 for adaptive non-uniform image scanning and acquisition based on time and spatial ROI selection. X-ray radiation exposure and image scanning parameters (timing, spatial ROI) are tuned, adjusted and controlled automatically or in response to user command. Cardiac function based gating and synchronizing signals include directly measured patient signals and derived trigger signals (such as frequency, energy, spectrum, dominant time/frequency signal components). Imaging system 25 is initialized in step 203 and performs self test and acquires a pre-scanning image and synchronizes patient functions signals (in order for accurate and precise phase lock and synchronization between different hardware and systems) in step 205. In response to system 61 processing the acquired pre-scan image or in response to user data entry in step 213, synchronization processor 23 in step 207 automatically selects a spatial ROI area.

Figure 3:
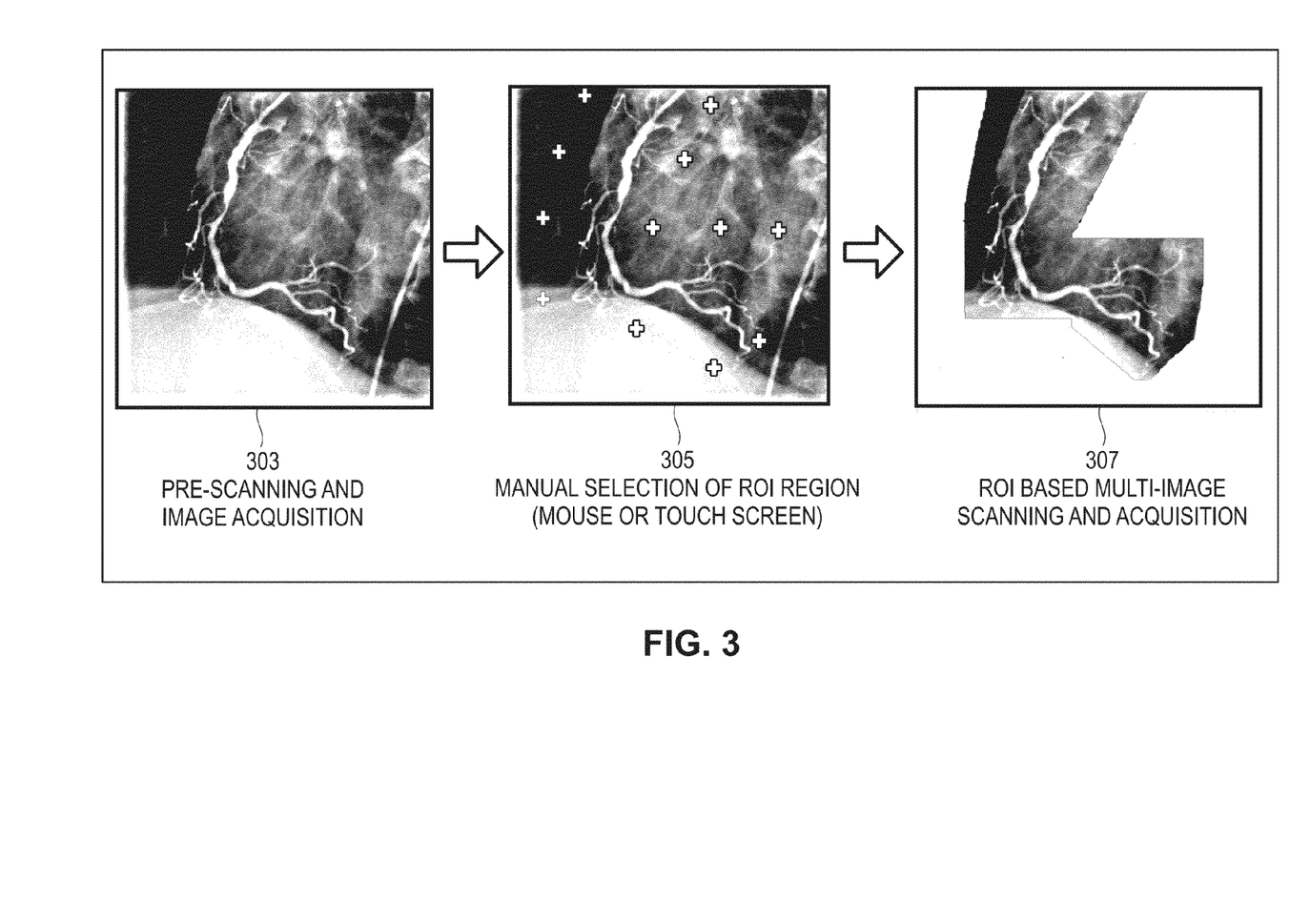
FIG. 3 illustrates manual selection of a ROI for X-ray exposure and image acquisition, according to invention principles.

FIG. 3 illustrates manual selection of a ROI for X-ray exposure and image acquisition. Pre-scan image 303 is acquired by imaging system 25 with a low radiation dose to obtain a rough picture of an image study area, tissue and organ position for use in selection of a ROI. A user determines the spatial size and ROI for X-ray imaging by manual selection of an area in the pre-scan image using a computer mouse or touch screen, for example, as illustrated in images 305 and 307. In another embodiment, image processing system 61 automatically determines the ROI based on image feature recognition such as vessel or chamber recognition using known image feature shape and feature image luminance transition edge detection in response to data indicating an anatomical feature to be imaged.

Patient monitoring system 49 acquires, buffers and digitizes patient monitoring signals including EP, hemodynamic and vital sign signals in step 233 for processing in step 236 to derive cardiac function signals including P, QRS, T, U wave portions of an ECG signal as well as to derive signals indicative of portions of blood pressure, SPO2 and respiratory signals, for example. Synchronization processor 23 in step 239 automatically determines a cardiac function trigger for image acquisition timing. Synchronization processor 23 in step 209 derives image acquisition trigger signals in response to cardiac function trigger for timing and a selected spatial ROI area. The cardiac function trigger and spatial ROI area are selected in response to predetermined selected configuration data of a physician or configuration data associated with a particular clinical procedure, diagnosis or imaging characteristic, and data indicating a type of clinical procedure and/or user entered data and commands provided in step 213.

Image acquisition device 25 in step 221 performs X-ray image acquisition of a selected spatial ROI area gated and synchronized using trigger signals derived in response to a cardiac function trigger. Specifically, device 25 in step 221 performs continuous non-uniform image scanning and acquisition, using timing and spatial information derived in response to ROI area edge determination (in one embodiment), X-ray collimator control, X-ray filtering control, non-uniform timing control and non-uniform X-ray intensity and dose control. In response to the selected ROI, controller 33 adjusts shape adaptive collimator 15 and X-ray radiation filter 27 for reduced dose image acquisition. The multi-part collimator 15 is used to construct different shapes to accommodate different ROIs. For example, an 8-pieces collimator is used to build more shapes for X-ray scanning than a 4 piece collimator.

Figure 4:
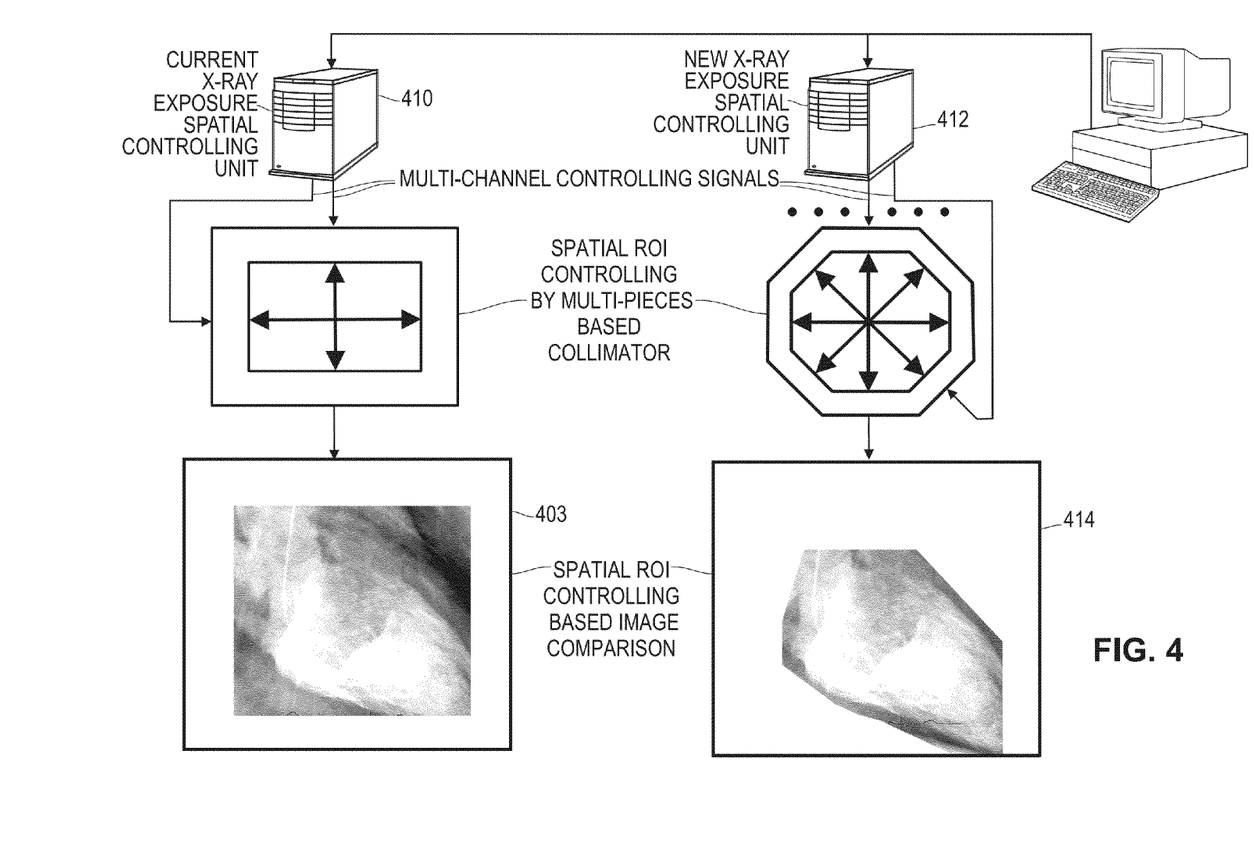
FIG. 4 shows an adaptively adjustable multi-piece collimator system used in X-ray radiation and exposure shaping and control, according to invention principles.

FIG. 4 shows an adaptively adjustable multi-piece collimator system used in X-ray radiation and exposure shaping and control. A known X-ray system typically employs a 2 direction control unit 410 and collimator 412 to provide a rectangular image 414. In contrast, the system 10 (FIG. 1) multi-piece collimator 15 (FIG. 1) is adjusted by controller 33 (FIG. 1) in 2-directions (XY) of planar movement as well as in rotation. In continuous image scanning, a different radiation dose and X-ray exposure shape is dynamically determined and controlled by unit 33. Multi-piece collimator 15 is dynamically adjusted at variable times to provide a ROI area that matches heart movement and dynamic heart shape and size, for example. At the same X-ray intensity and resolution and contrast, multi-piece collimator 15 limits the X-ray radiation in a specific ROI area to provide an approximate 45% radiation dose reduction, for example, as illustrated in the reduced area of image 403 related to image 414. The multiple pieces of collimator 15 are straight edged and similarly shaped in one embodiment. In another embodiment, the multiple pieces are different in size and shape. For example in cardiac heart function monitoring, a circle or angular shaped piece is used. Different kinds of collimator pieces and X-ray filter pieces are advantageously employed in response to data indicating a clinical application and usage.

In a clinical application, such as heart function and coronary artery vessel analysis, the heart is moving and resting periodically and has a dynamic moving phase and static phase. Due to these characteristics, a relatively slowly reacting collimator may be unable to switch between two fast moving images to adjust to a different ROI in a required time period. Hence the ROI area in one single image may be divided into different (non-uniform) radiation regions, a low dose region and high dose region. Non-uniform X-ray radiation is applied by using different X-ray filters 27 with predetermined shapes, such as for a whole heart, left ventricle, circle, triangle, which are selected by controller 33 in response to data identifying a clinical application. The X-ray radiation filter 27 thickness is also adaptively varied to control percentage of radiation dose reduction, such as by using a 30%, 50%, 75% dose limiter.

Figure 5:
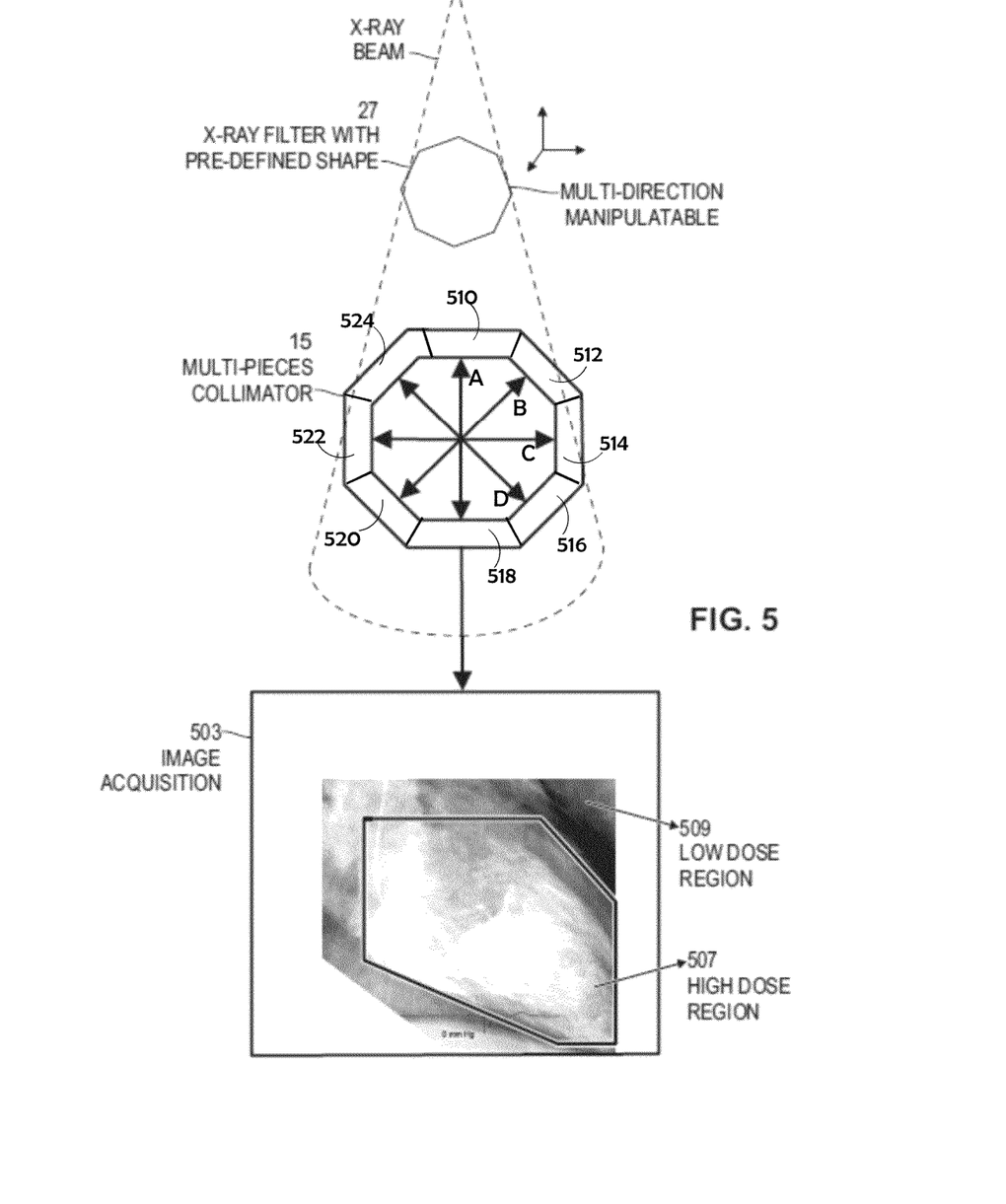
FIG. 5 shows non-uniform multi-piece radiation filtering image acquisition in response to spatial ROI area control, according to invention principles.

FIG. 5 shows use of non-uniform multi-piece radiation filter 27 (FIG. 1) in image acquisition in response to spatial ROI area control. System 10 (FIG. 1) employs programmable multi-piece X-ray radiation filter 27 together with multi-piece collimator 15 (FIG. 1) to provide non-uniform radiation exposure in acquisition of image 503. An X-ray beam passes through X-ray radiation filter 27 providing adaptive radiation attenuation over an image area and collimator 15 providing adaptive shape exposure. Shape adaptive collimator 15 includes multiple movable different portions of X-ray absorbent material 510, 512, 514, 516, 518, 522, 524, which are adjustable along arrows A, B, C, D, and adjusts dimensions of the spatial cross section of the X-ray beam of radiation. For example, filter 27 and collimator 15 are adaptively configured to provide a high radiation dose region in a ROI associated with dynamic heart activity and a low radiation dose region in the ROI for comparison, such as for function and movement analysis. Alternatively, the high and low doses may be applied to different areas within a ROI. High radiation dose region 507 in image 503 has full X-ray radiation exposure (e.g., 100%) while low radiation dose region 509 receives partial X-ray radiation exposure (e.g., 45%) since the low dose region is of less clinical interest.

Returning to FIG. 2, image processing system 61 in step 222 aligns (registers) sequential images and detects abnormalities and performs diagnosis and characterization of abnormal cardiac functions and pathologies in response to an image calculation method selected in step 223. Specifically, in step 223 image processing system 61 selects a process to use for analysis of an acquired image to determine, medical condition, severity, time step used between image acquisition, chamber volume and to derive a 3D image reconstruction from a 2D image, for example. The analysis also determines cardiac function (e.g. stroke volume, cardiac output, time synchronization) parameters, and performs a standard deviation analysis.

In step 225 image processing system 61 uses a selected process to analyze an acquired image to determine image associated parameters and calculate image associated values and identify a particular medical condition by mapping determined parameters and calculated values to corresponding value ranges associated with medical conditions using mapping information in repository 17. Image processing system 61 in step 231 also determines medical condition severity, chamber volume and derives a 3D image reconstruction from a 2D image, for example. Steps 222 and 225 are iteratively repeated in response to manual or automatic direction in step 228 to identify medical condition characteristics in one or more different acquired images. In response to completion of iterative image analysis of steps 222, 225 and 228, processor 61 in step 231 determines location, size, volume, severity and type of medical condition as well as a time within a heart cycle associated with a medical condition. Processor 61 initiates generation of an alert message for communication to a user in step 237 and provides medical information for use by a physician in making treatment decisions. Display processor 26 in step 233 NO presents images, acquired by acquisition device 25 to a user on a reproduction device such as display 19 or a printer and stores images in repository 17.

In order to achieve improved image quality presenting a patient ROI in adequate detail with lowest radiation exposure to the patient, system 10 acquires an image of an adaptively selected ROI in combination with synchronized radiation emission and image acquisition. A synchronized and spatially adapted patient image acquisition mode is determined in response to selection of a ROI in a pre-scan image. In one embodiment, in response to selection of a ROI (for example, a left ventricle), a user or processor 61 adaptively and automatically selects blood pressure based image acquisition synchronization. In another example, a user initiates monitoring and evaluation of cardiac output of a left ventricle (as shown in the FIG. 6). Processor 61 uses an image luminance transition edge (boundary) detection method to detect shape and size of a left ventricle and automatically select a ROI based on a left ventricle boundary. Processor 61 in conjunction with controller 33 adjusts X-ray multi-piece collimator 15 and radiation filter 27 to best match a selected ROI and initiates controlled radiation exposure in response to user command. Processor 61 in conjunction with controller 33 and synchronization processor 23 employs non-uniform gated image acquisition of a QRST portion of an ECG heart cycle to capture fast heart activity of a left ventricle and another waveform portion to trigger a slow rest phase of a left ventricle. Processor 61 in conjunction with controller 33 and synchronization processor 23, employs a P wave to trigger image acquisition of fast activity of a left atrium and another waveform portion for triggering image acquisition of slow activity of a left atrium.

Figure 6:
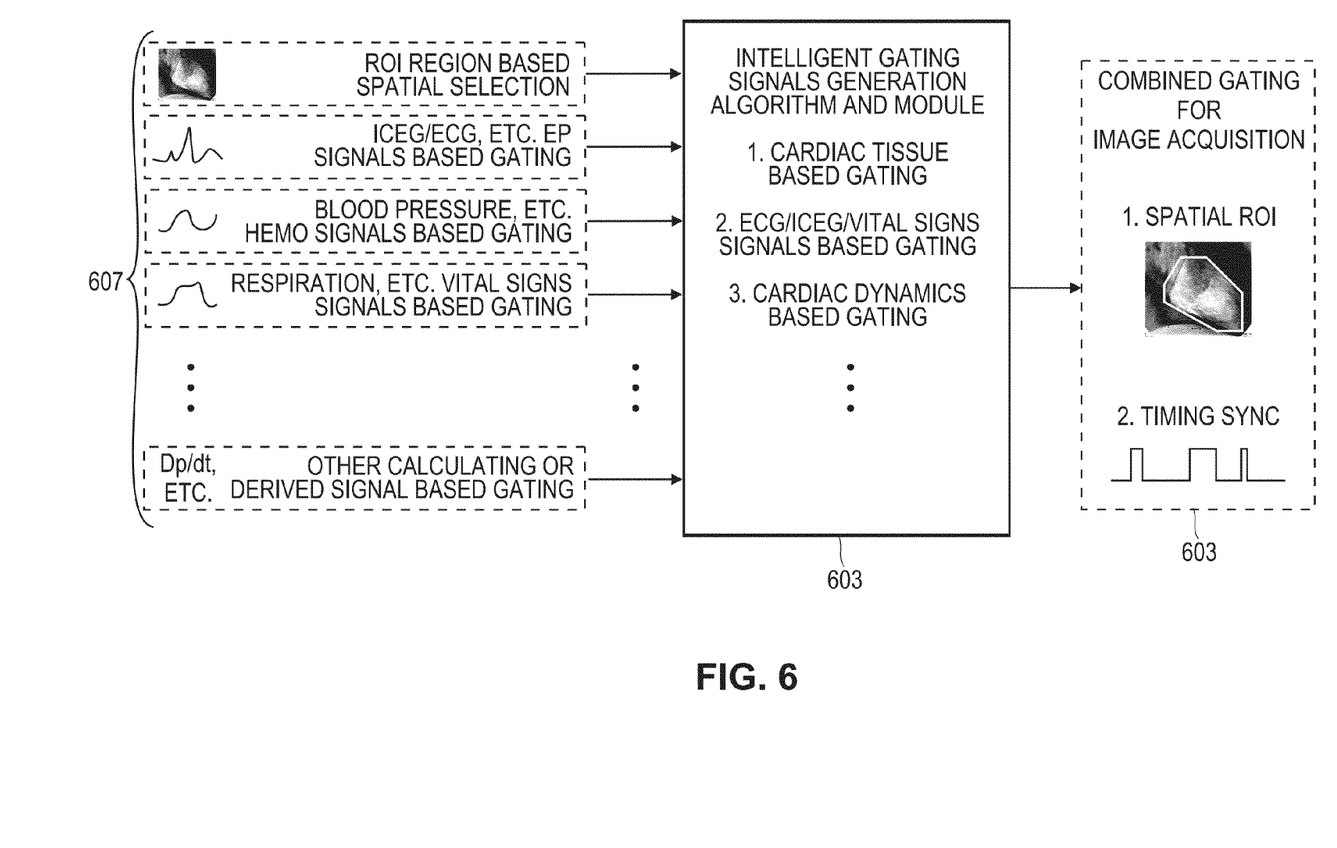
FIG. 6 shows adaptively timed image gating and spatial signal generation based on ROI and EP (electrophysiological), Hemodynamic and Vital sign signals, and associated derived signals, according to invention principles.

FIG. 6 shows adaptively timed image gating and spatial signal 609 generation by unit 603 (provided by units 23, 33 and 61 (FIG. 1), for example) based on ROI and EP (electrophysiological), Hemodynamic and Vital sign signals 607, and associated derived signals. Processor 61 uses data indicating imaging study scope and target anatomical region and admitting diagnosis to associate cardiac function with a ROI and an image acquisition trigger pattern, such as using a P wave trigger to capture left atrial activity and function. X-ray imaging system 25 (FIG. 1) (including a sensor, emitter, motor) and acquisition control unit are configured based on the determined spatial region selection and image acquisition trigger pattern and clinical application. This improves procedure effectiveness and reduces patient risk.

Figure 7:
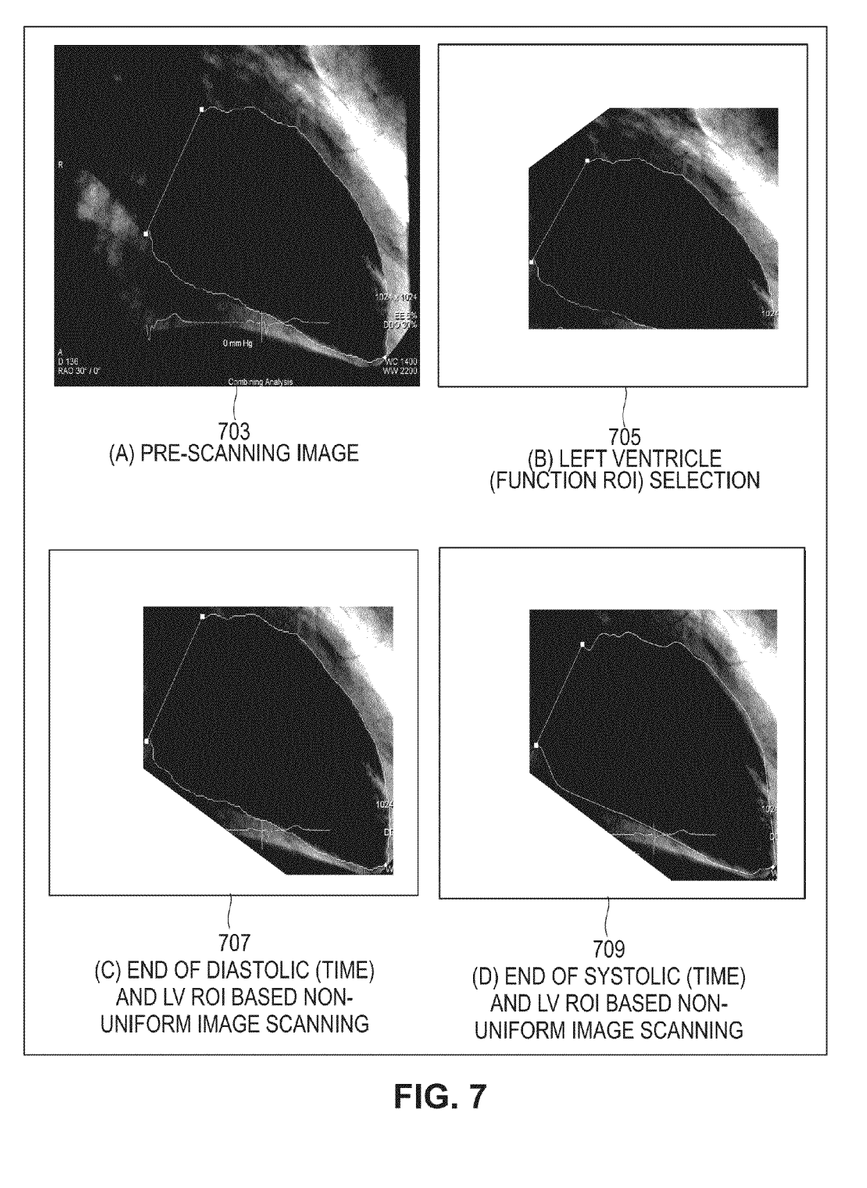
FIG. 7 shows left ventricle (LV) cardiac output image scanning using non-uniform timing and spatial ROI selection, according to invention principles.

FIG. 7 illustrates left ventricle (LV) cardiac output image scanning using non-uniform timing and spatial ROI selection for cardiac output (CO) and stroke volume (SV) calculation and monitoring. A user selects a ROI boundary such as of a LV area in low radiation dose pre-scan cardiac image 703 acquired by system 25 (FIG. 1). Image 705 shows the selected ROI boundary optimized for LV reduced radiation dose image scanning. In another embodiment, the ROI boundary demarcating an LV area is automatically selected by processor 61 using luminance transition edge detection. Processor 61 and controller 33 determine a ROI and synchronization processor 23 determines image acquisition gating synchronization signals for individual images for LV function analysis. Processor 23 generates image acquisition gating synchronization signals involving determination of an X-ray scanning trigger signal protocol to capture images of the maximum and minimum LV volume. The generated image acquisition gating synchronization signals are used for acquisition of individual images for LV function analysis and in particular for acquisition of an end of Diastolic phase image 707 and end of systolic phase image 709. Images 707 and 709 are analyzed by processor to calculate cardiac SV (stroke volume).

In response to a determined type of clinical application, system 10 adaptively selects synchronization trigger signal timing from multiple synchronization arrangements using cardiac function signal based image acquisition. The trigger signals enables adaptive variation in timing of image acquisition within successive heart cycles of each individual image frame of multiple sequential image frames. In order to characterize cardiac function (such as for chamber and tissue evaluation of cardiac patients who have hypertension), system 10 enables acquisition of a single image to diagnose hypertension effects. Thereby system 10 reduces complexity of a corresponding medical procedure and associated risk of radiation overdose.

Figure 8:
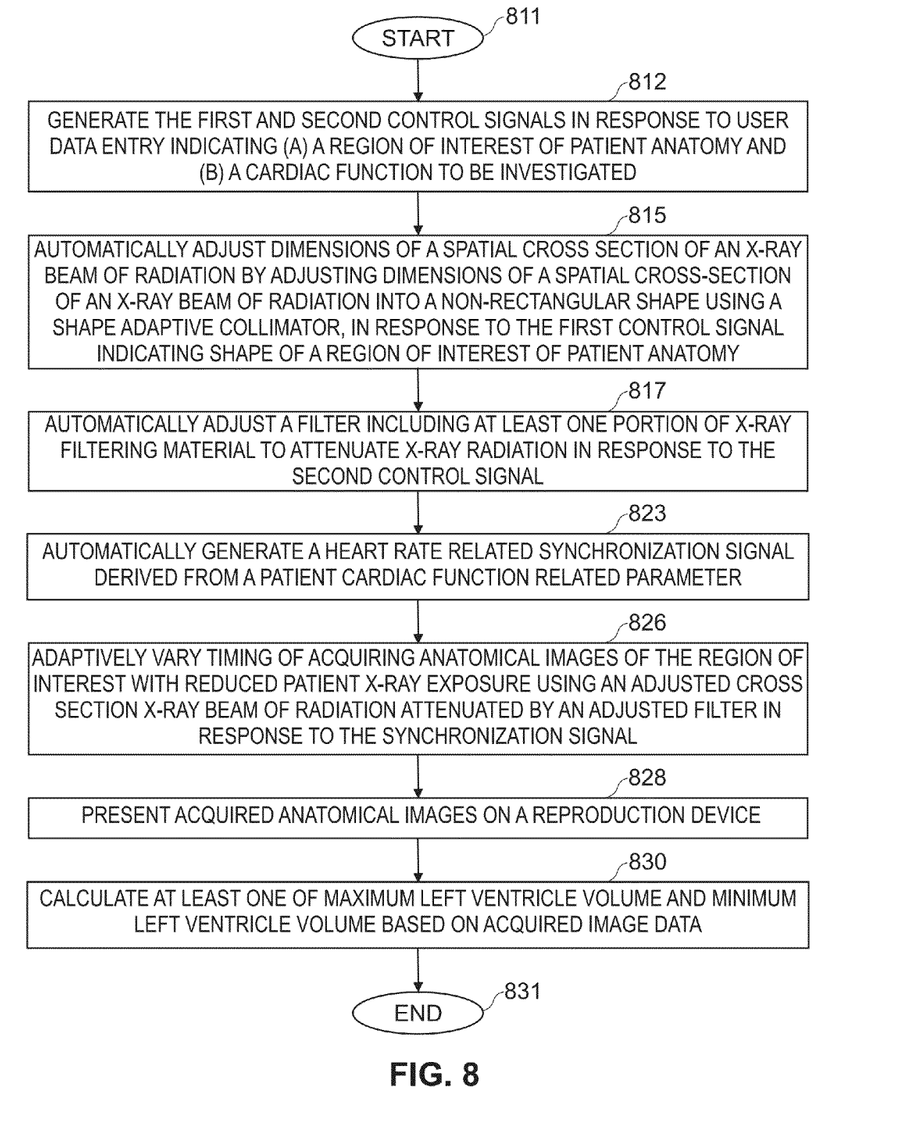
FIG. 8 shows a flowchart of a process used by a medical imaging system for adaptively acquiring anatomical images, according to invention principles.

FIG. 8 shows a flowchart of a process used by medical imaging system 10 (FIG. 1) for adaptively acquiring anatomical images. In step 812 following the start at step 811, controllers 33 generate first and second control signals in response to user data entry indicating, (a) a region of interest of patient anatomy and (b) a cardiac function to be investigated. Shape adaptive collimator 15 in step 815 automatically adjusts dimensions of a spatial cross section of an X-ray beam of radiation in response to the first control signal. Shape adaptive collimator 15 includes multiple automatically movable different portions of X-ray absorbent material and automatically adjusts dimensions of the spatial cross section of the X-ray beam of radiation into a non-rectangular shape, in response to the first control signal indicating shape of a region of interest of patient anatomy. Collimator 15 adaptively adjusts at least three separately and relatively movable parts with at least two parts being mutually angularly adjustable to adapt the shape adaptive collimator to alter the dimensions of the spatial cross section of the X-ray beam to an irregular shape. In step 817 controller 33 automatically adjusts a filter (comprising a semi-transparent filter in one embodiment) including at least one portion of X-ray filtering material to attenuate X-ray radiation in response to the second control signal. Controller 33 automatically adjusts the position of the portion of X-ray absorbent material and the X-ray filtering material in response to the first and second control signals.

In step 823 synchronization processor 23 automatically generates a heart rate related synchronization signal derived from a patient cardiac function related parameter. The patient cardiac function related parameter is a blood flow related parameter and the blood flow related parameter indicates at least one of (a) invasive blood pressure, (b) non-invasive blood pressure, (c) blood flow velocity, (d) blood flow acceleration, (e) blood flow frequency and (f) a blood pressure gradient indicator. In one embodiment, the heart rate related synchronization signal comprises a signal synchronized with end-diastolic pressure in a cardiac cycle. The end-diastolic pressure synchronized signal is derived from a non-invasive blood pressure monitoring device or and ECG signal and is derived from a blood oxygen saturation (SpO2) monitoring device. In a further embodiment, the heart rate related synchronization signal comprises a signal synchronized with end-systolic pressure in a cardiac cycle and is derived from a non-invasive blood pressure monitoring device.

Processor 23 adaptively varies timing of image acquisition within an individual heart cycle and between successive heart cycles of each individual image frame of multiple sequential image frames. In step 826, imaging system 25 adaptively varies timing of acquiring anatomical images of the region of interest with reduced patient X-ray exposure using an adjusted cross section X-ray beam of radiation attenuated by an adjusted filter in response to the synchronization signal. Image acquisition device 25 adaptively selects image pixel resolution of individual image frames of the multiple sequential image frames in response to data identifying a heart cycle segment so that successively acquired image frames have different image pixel resolution within a single heart cycle. Display processor 63 presents, at step 828, acquired anatomical images on reproduction device 19 and provides at least one display image enabling a user to enter data indicating a shape of a region of interest of patient anatomy using an image of the patient anatomy. Image processor 39 in step 830 calculates at least one of maximum left ventricle volume and minimum left ventricle volume based on acquired image data. The process of FIG. 8 terminates at step 831.

A processor as used herein is a device for executing machine-readable instructions stored on a computer readable medium, for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a computer, controller or microprocessor, for example, and is conditioned using executable instructions to perform special purpose functions not performed by a general purpose computer. A processor may be coupled (electrically and/or as comprising executable components) with any other processor enabling interaction and/or communication therebetween. A user interface processor or generator is a known element comprising electronic circuitry or software or a combination of both for generating display images or portions thereof. A user interface comprises one or more display images enabling user interaction with a processor or other device.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A user interface (UI), as used herein, comprises one or more display images, generated by a user interface processor and enabling user interaction with a processor or other device and associated data acquisition and processing functions.

The UI also includes an executable procedure or executable application. The executable procedure or executable application conditions the user interface processor to generate signals representing the UI display images. These signals are supplied to a display device which displays the image for viewing by the user. The executable procedure or executable application further receives signals from user input devices, such as a keyboard, mouth, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity.

The system and processes of FIGS. 1-8 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. The system employs spatial region based image control and scanning to reduce a patient X-ray radiation dose by controlling the ROI imaged and improve image resolution. Further, the processes and applications may, in alternative embodiments, be located on one or more (e.g., distributed) processing devices on a network linking the units of FIG. 1. Any of the functions and steps provided in FIGS. 1-8 may be implemented in hardware, software or a combination of both.

What is claimed is:

1. A medical imaging system for adaptively acquiring anatomical images, comprising:
    a programmable image radiation filter and a shape adaptive collimator including a plurality of different portions of X-ray absorbent material automatically adjustable to alter the dimensions of a spatial cross section of an X-ray beam of radiation into a non-rectangular shape, in response to a first control signal indicating shape of a region of interest of patient anatomy, wherein the programmable image radiation filter and the shape adaptive collimator are configured to provide a non-uniform image radiation exposure by adjusting X-ray beam shape, focus and intensity;
    the shape adaptive collimator adaptively configured to simultaneously provide a high radiation dose to a first area within the region of interest and a low radiation dose to a second area within the region of interest;
    a synchronization processor for providing a heart rate related synchronization signal derived from a patient cardiac function related parameter, said synchronization signal enabling adaptive variation in timing of image acquisition within an individual heart cycle and between successive heart cycles of each individual image frame of a plurality of sequential image frames;
    an X-ray image acquisition device using said shape adaptive collimator for acquiring anatomical images of said region of interest with reduced patient X-ray exposure in response to said synchronization signal; and
    a display processor for presenting images, acquired by said acquisition device to a user on a reproduction device.

2. The system according to claim 1, wherein said shape adaptive collimator employs at least three separately and relatively movable parts with at least two parts being mutually angularly adjustable to adapt said collimator to alter the dimensions of a spatial cross section of said X-ray beam to an irregular shape.

3. The system according to claim 1, the programmable image radiation filter including at least one portion of X-ray filtering material automatically adjustable to attenuate X-ray radiation in response to a second control signal.

4. The system according to claim 3, including a controller for generating the first and second control signals in response to user data entry indicating, (a) a region of interest of patient anatomy and (b) a cardiac function to be investigated.

5. The system according to claim 4, wherein said controller automatically adjusts the position of said portion of X-ray absorbent material and said X-ray filtering material in response to said first and second control signals.

6. The system according to claim 1, wherein said display processor provides at least one display image enabling a user to enter data indicating a shape of a region of interest of patient anatomy using an image of the patient anatomy.

7. The system according to claim 1, wherein said image acquisition device adaptively selects image pixel resolution of individual image frames of said plurality of sequential image frames in response to data identifying a heart cycle segment so that successively acquired image frames have different image pixel resolution within a single heart cycle.

8. The system according to claim 1, wherein said heart rate related synchronization signal comprises a signal synchronized with end-diastolic pressure in a cardiac cycle.

9. The system according to claim 8, wherein the end-diastolic pressure synchronized signal is derived from at least one of a non-invasive blood pressure monitoring device and ECG signal.

10. The system according to claim 8, wherein the end-diastolic pressure synchronized signal is derived from a blood oxygen saturation (SpO2) monitoring device.

11. The system according to claim 1, wherein said heart rate related synchronization signal comprises a signal synchronized with end-systolic pressure in a cardiac cycle.

12. The system according to claim 11, wherein the end-systolic pressure synchronized signal is derived from a non-invasive blood pressure monitoring device.

13. The system according to claim 1, wherein said patient cardiac function related parameter is a blood flow related parameter, and said blood flow related parameter indicates at least one of, (a) invasive blood pressure, (b) non-invasive blood pressure, (c) blood flow velocity, (d) blood flow acceleration and (e) blood flow frequency.

14. The system according to claim 13, wherein said patient blood flow related parameter is a blood pressure gradient indicator.

15. The system according to claim 1, including an image processor for calculating at least one of maximum left ventricle volume and minimum left ventricle volume based on acquired image data.

16. A method employed by a medical imaging system for adaptively acquiring anatomical images, the method comprising:
    automatically adjusting dimensions of a spatial cross section of an X-ray beam of radiation into a non-rectangular shape using a programmable image radiation filter and a shape adaptive collimator, in response to a first control signal indicating shape of a region of interest of patient anatomy, said shape adaptive collimator including a plurality of automatically movable different portions of X-ray absorbent material, wherein the programmable image radiation filter and the shape adaptive collimator are configured to provide a non-uniform image radiation exposure by adjusting X-ray beam shape, focus and intensity;
    simultaneously providing a high radiation dose to a first area within a region of interest and a low radiation dose to a second area within the region of interest;
    automatically generating a heart rate related synchronization signal derived from a patient cardiac function related parameter, said synchronization signal enabling adaptive variation in timing of image acquisition within an individual heart cycle and between successive heart cycles of each individual image frame of a plurality of sequential image frames;
    adaptively varying timing of acquiring anatomical images of said region of interest with reduced patient X-ray exposure using an adjusted X-ray beam of radiation having a non-rectangular shape in response to said synchronization signal; and
    presenting acquired anatomical images on a reproduction device.

17. The method according to claim 16, wherein adaptively adjusting at least three separately and relatively movable parts with at least two parts being mutually angularly adjustable to adapt said shape adaptive collimator to alter the dimensions of a spatial cross section of said X-ray beam to an irregular shape.

18. The method according to claim 16, including the step of automatically adjusting programmable image radiation filter including at least one portion of X-ray filtering material to attenuate X-ray radiation in response to a second control signal.

19. A method employed by a medical imaging system for adaptively acquiring anatomical images, the method comprising:
    automatically adjusting dimensions of a spatial cross section of an X-ray beam of radiation in response to a first control signal;
    automatically adjusting a shape adaptive collimator and a programmable image radiation filter including at least one portion of X-ray filtering material to attenuate X-ray radiation in response to a second control signal, wherein the programmable image radiation filter is configured to provide a non-uniform image radiation exposure by adjusting X-ray beam shape, focus and intensity;
    automatically generating a heart rate related synchronization signal derived from a patient cardiac function related parameter, said synchronization signal enabling adaptive variation in timing of image acquisition within an individual heart cycle and between successive heart cycles of each individual image frame of a plurality of sequential image frames;
    simultaneously providing a high radiation dose to a first area within a region of interest and a low radiation dose to a second area within the region of interest;
    adaptively varying timing of acquiring anatomical images of said region of interest with reduced patient X-ray exposure using an adjusted cross section X-ray beam of radiation attenuated by the programmable image radiation filter in response to said synchronization signal; and
    presenting acquired anatomical images on a reproduction device.

20. The method according to claim 19, including the step of automatically adjusting dimensions of a spatial cross section of an X-ray beam of radiation into a non-rectangular shape using the shape adaptive collimator, in response to said first control signal indicating shape of a region of interest of patient anatomy, said shape adaptive collimator including a plurality of automatically movable different portions of X-ray absorbent material, wherein the shape adaptive collimator is configured to contribute to providing the non-uniform image radiation exposure by further adjusting X-ray beam shape, focus and intensity.

21. The method according to claim 20, including the step of adaptively adjusting at least three separately and relatively movable parts with at least two parts being mutually angularly adjustable to adapt said shape adaptive collimator to alter the dimensions of said spatial cross section of said X-ray beam to an irregular shape.

* * * * *